US005433604A

United States Patent [19]
Landgraf

[11] Patent Number: 5,433,604
[45] Date of Patent: Jul. 18, 1995

[54] MEDICAL INSTRUMENT HAVING AN INTERNALLY-COOLED TOOL

[75] Inventor: Hermann Landgraf, Lorsch, Germany

[73] Assignee: Siemens Aktiengesellschaft, Munich, Germany

[21] Appl. No.: 196,471

[22] Filed: Feb. 15, 1994

[30] Foreign Application Priority Data
Feb. 15, 1993 [DE] Germany .......... 43 04 514.6

[51] Int. Cl.6 .............................................. A61C 1/12
[52] U.S. Cl. ...................................... 433/82; 433/104
[58] Field of Search ................ 433/82, 104, 165, 166; 408/57, 59; 51/356

[56] References Cited
U.S. PATENT DOCUMENTS

| 3,624,905 | 2/1970 | Barsby | 433/82 |
| 3,762,052 | 10/1973 | Melde | 433/165 |
| 3,871,097 | 3/1975 | Melde | 433/165 |
| 4,021,920 | 5/1977 | Kirschner et al. | 433/165 |
| 5,096,421 | 3/1992 | Seney | 433/165 |
| 5,275,558 | 1/1994 | Seney | 433/82 |

FOREIGN PATENT DOCUMENTS

| 0374276 | 6/1990 | European Pat. Off. . |
| 0455452 | 11/1991 | European Pat. Off. . |
| 2331023 | 12/1977 | Germany . |
| 4039162 | 6/1992 | Germany . |

Primary Examiner—Cary E. O'Connor
Attorney, Agent, or Firm—Hill, Steadman & Simpson

[57] ABSTRACT

A medical instrument, particularly a dental instrument has a head housing with a chucking arrangement for gripping an internally-cooled tool. In order to assume an optimum transfer of coolant from a delivery channel into an internal channel of the tool, an exit opening of the delivery channel is arranged opposite the admission opening of the tool in a no-contact fashion at the end of the tool being gripped. To prevent leakage, sealing gaps are provided between the moving parts in the head housing and compressed air is charged into these sealing gaps under a higher pressure in comparison to the pressure of the coolant.

17 Claims, 3 Drawing Sheets

MEDICAL INSTRUMENT HAVING AN INTERNALLY-COOLED TOOL

BACKGROUND OF THE INVENTION

The present invention is directed to medical instrument, particularly to a dental instrument having a hollow shaft which is rotatably seated in a head housing for the acceptance of a chucking means of a fixture for an internally-cooled tool which has a longitudinal channel for delivery of a coolant to an end of the tool, the instrument having a delivery channel for delivering coolant to an admission opening of the longitudinal channel at an end face of the shaft in a non-contacting fashion.

European Patent Application 0 455 452-A1 discloses a dental handpiece having a chucking means for receiving a tool having a hollow longitudinal channel. The handpiece also has a delivery channel for delivering cooling water to an admission opening of the tool in a free jet without contact therewith. Moreover, a part of the drive air which is conducted out of the instrument via an exhaust channel as exhaust or return air after flowing through the turbine drive is conducted through a ball bearing arrangement into a space wherein a pump member rotating together with the hollow shaft is located. Worm-shaped baffles are located in the inside of the housing for the pump member, and these baffles pump the extracted exhaust air into the channel of the tool. Used exhaust air, which usually also has dirt particles and lubricants included in it, is conducted into the longitudinal channel of the tool by this pump means. Apart from the fact that this is extremely undesirable for hygienic reasons, such an arrangement also has other disadvantages. The pump action, thus, only occurs when the exhaust air is fully available, for example when the turbine is rotating at an adequate speed. Given standstill of the tool or given a plugged exit opening at the tool as well, it can easily occur that the supplied coolant, usually water, will be pressed back through the pump arrangement and, thus, into the bearings.

A further disadvantage of such an embodiment may be seen wherein the arrangement is suitable for only one rotational sense of the tool. Given a change in rotational direction or sense, an undesirable suction effect could occur instead of the pump effect.

U.S. Pat. No. 4,021,920, whose disclosure is incorporated herein by reference thereto and which claims priority from German Application 23 31 023, discloses an arrangement wherein the delivery tube for the coolant is immersed into the longitudinal channel of the tool when the tool is put in place. A sealing ring is arranged in the tool to provide sealing of the cooling water from the remaining parts of the head housing. Such an embodiment has the disadvantage that the seal produces relatively high friction between the tool and the stationary delivery tube and will result in the useful life of the tool being shortened. Moreover, such a coolant delivery is only suitable for extremely low speeds. Another disadvantage may be seen wherein the instrument can only be employed for internally-cooled drills and that drills and instruments must be structurally matched to one another.

U.S. Pat. No. 5,096,421, whose disclosure is incorporated herein by reference thereto, discloses another design wherein the delivery of the coolant occurs in the region of the pressure cover of the treatment head. A membrane, which is provided with a bore, is clamped in a chamber of the head housing between the exit opening of the delivery channel and the admission opening in the tool shaft. This membrane presses in a sealing fashion against the end face of the tool shaft during operation, wherein the tool rotates, and this tends to create a seal with respect to the remaining housing parts, particularly the bearings for the hollow shaft.

The disadvantage of this arrangement is also present because a relatively high wear is established as a consequence of the friction between the drill shaft and membrane. In addition, an adequately reliable separation of the cooling path from the neighboring ball bearings is not established. Thus, the coolant can proceed into the bearings or, respectively, oil can proceed from the bearings into the longitudinal channels of the tool.

SUMMARY OF THE INVENTION

The present invention is directed to an improvement in a medical instrument, particularly a dental instrument, wherein an optimum transfer of coolant onto the rotating tool is enabled while avoiding the above-mentioned disadvantages, particularly seals that cause friction and are subject to wear. The arrangement also should be fashioned so that the instrument can also be operated with normal tools, for example those tools which are not internally cooled and without a structural modification.

To accomplish these goals, the present invention is directed to a medical instrument comprising a head housing having means for mounting a hollow shaft for rotating in the housing, said shaft having chucking means for gripping one end of an internally-cooled tool, said tool having an axially extending channel extending from an admission opening at the one end to an exit opening at the opposite end of the tool, said housing having a first delivery channel being connected to a source of coolant and having an exit opening residing opposite to the admission opening of the tool in the chucking means in a non-contacting manner, sealing gaps being provided between the rotating parts of the chucking means adjacent the one shaft end of the tool, a second delivery channel extending concentric relative to the first delivery channel and being connected to a source of compressed air under high pressure in comparison to the pressure of the coolant to supply compressed air to the sealing gaps to prevent leakage of the coolant.

The invention is based on the perception that an adequate sealing both relative to the coolant side as well as relative to the exhaust air side or, respectively, to the atmosphere given minimum air consumption can be achieved by the arrangement of suitable sealing gaps with the assistance of clean fresh air.

Other advantages and features of the invention will be readily apparent from the following description of the preferred embodiments, the drawings and claims.

DESCRIPTION OF THE PREFERRED EMBODIMENTS

Figure 1:
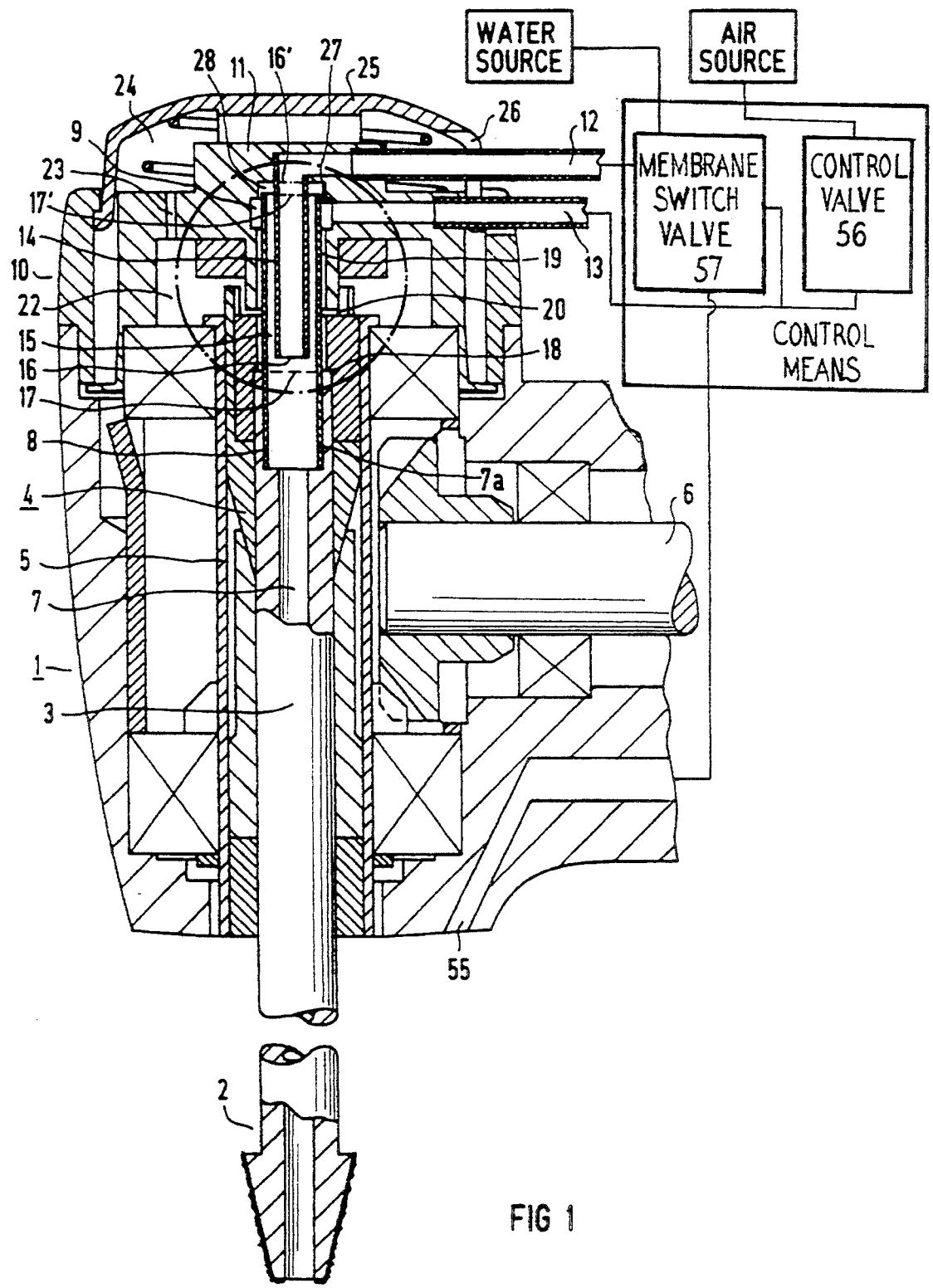
FIG. 1 is a cross sectional view of a head housing with portions in elevation for purposes of illustration in accordance with the present invention.

The principles of the present invention are particularly useful when incorporated in a medical instrument, such as a dental instrument, having a head housing 1 which receives a drilling tool 2 that is rotatably seated in a known way. The tool 2 has its shaft 3 held in a chucking fixture or means 4 that engages one end of the tool. The chucking fixture 4 is, in turn, mounted in a hollow shaft 5 which can be placed in rotation in a known way by gearing parts which are rotated by a shaft 6. Since the drive and bearing of the hollow shaft, as well as the chucking fixture in the head housing, are well known in the prior art, a further description of these devices is not included herein.

The tool 2 contains a through longitudinal channel or cooling channel 7 that discharges in the region of the tip of the tool at a suitable location of the active work surface and which is illustrated as being in the axial direction in the illustrated embodiment. The diameter of the longitudinal channel 7 is somewhat larger in a region adjacent the opposite end of the tool because of a counterbore 7a. A small tube 8 is received in the counterbore 7a and projects beyond the end of the shaft 5 and the end of the tool and as may be seen from the drawing, in the assembled condition the tube 8 projects into an air distributor space 9 of the upper housing part 10. The small tube 8 is a component part of the tool and can be either put in place in a suitable way in the counterbore end of the tool or can also be an integral component part of the tool.

The upper housing part 10 contains housing pans 11, wherein, first, a coolant conduit 12 and a compressed air delivery channel 13 are conducted. The lines from the corresponding sources of pressurized agent to the head housing can be conducted either externally as well as internally in the instrument. A suitable coolant, preferably water, is brought to the head housing via the line 12 from a water source and, as may be seen from the drawing, is aligned centrally relative to the tool axis and is concentrically surrounded by the small tube 8 in the mounted condition of the tool 2. The arrangement is undertaken so that a relatively narrow gap 15 having a relatively great length is formed between the two parts, and this gap, which shall be set forth in greater detail hereinbelow, effects a sealing on the basis of the supplied compressed air relative to the coolant side, i.e., toward the water side.

The compressed air line 13 is connected to a compressed air source and is connected to the above-mentioned air distribution space 9 which merges into the above-mentioned gap 15. The arrangement is undertaken so that the exit opening 16 of the section 14 is positioned opposite the admission opening 17, indicated with broken lines, when the small tube 8 is not inserted in the counterbore 7a of the channel 7. The spacing between the exit opening 16 and admission opening 17 defines a space of less than 1 mm. The transfer of the coolant thus occurs in a non-contacting fashion, namely both with a well as without the small tube 8 put in place. The spacing is defined by a detent or shoulder 18 in the chucking fixture or means 4.

As already mentioned, the compressed air supplied via the line 13 serves as the sealing air for sealing both relative to the coolant, i.e., the water, as well as relative to the exhaust air and atmosphere. The distributor space 9 thereby sees to a uniform distribution of the compressed air at the sealing gap. The compressed air initially introduced into the distributor space 9 is partially conducted to the above-mentioned gap 15 and forms an adequate seal vis-a-vis the supply water thereat. The other part of the compressed air is conducted to additional gaps, such as 19 and 20, and this part of the air serves the purpose of sealing from the outside or from the atmosphere. The aeration occurs via a chamber 22, an aeration channel 23, a space 24, which is formed by the housing cover 25 and a housing part 11 and, finally, via an opening 26. Other paths that eliminate excess sealing air or air leakage are also conceivable instead of the above-described path.

The gap 19 that extends parallel to the axis has a relatively tight tolerance in comparison to the radial annular map 20. The pump effect which is intrinsically undesirable can be reduced by selecting a relatively large gap at the annular gap 20.

A reliable transfer of the media without the above-mentioned disadvantages present in the prior art is guaranteed in combination with the disclosed arrangement of the small tube which provides a transfer of the coolant into the tool close to the rotational axis and given the smallest diameter.

The design which has been present allows a tool without longitudinal channels, i.e., a tool that is not internally cooled, to be utilized both with connected as well as with disconnected water supply without structural modifications having to be undertaken for this purpose. In a preferred modification of this embodiment the section 14 doesn't dip into the tubular part 8 as illustrated in FIG. 1 but ends in an exit opening 16'. This exit opening 16' resides opposite the admission opening 17' of the tube 8. The end portion of tubular part 8 and the air distribution space 9 defines a further small gap 27. This gap 27 separates space 9 from a space 28 which in this modification is connected (via exit opening 16') with the coolant conduit 12 when compressed air is introduced into space 9.

Additional modifications or embodiments of the invention are illustrated in FIGS. 2–5 and are namely in the region indicated in broken lines in FIG. 1.

Figure 2:
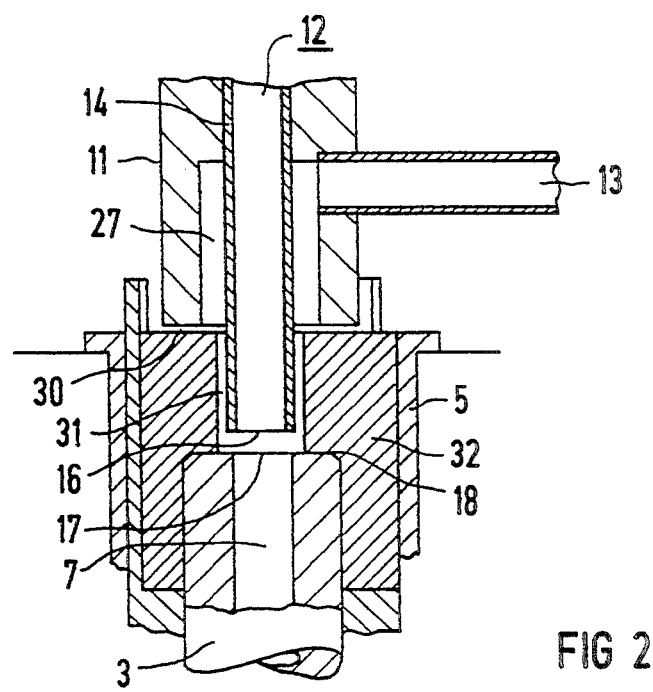
FIG. 2 is a partial cross sectional view taken in the area of the broken line circle of FIG. 1 of a second embodiment of the present invention.

In the second embodiment of FIG. 2, the shaft of the tool has a longitudinal channel 7 that remains constant in diameter. The line section of the delivery channel 12 for the coolant ends immediately above the admission opening 17 of the longitudinal channel 7 so that the exit opening 16 and the admission opening 17 reside opposite one another in a corresponding fashion and at a slight distance from one another.

Here, too, the compressed air is first conducted into a distributor space 27 and then charges radially and axially parallel sealing gaps 30 and 31. The radial sealing gap 30 is formed by planar end faces of the housing part 11 and by a sleeve 32, which is part of the chucking fixture 4. The axially parallel gap 31 also has relatively tight tolerances here, so that little air is mixed with the supplied coolant.

Figure 3:
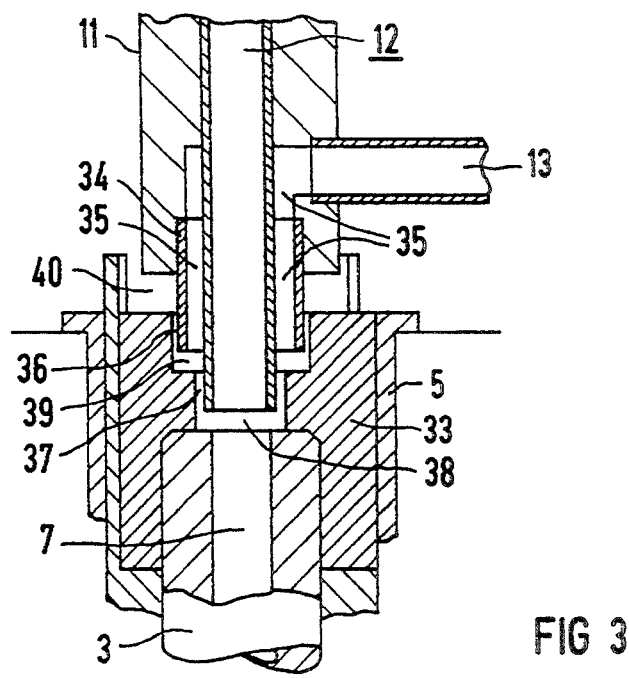
FIG. 3 is a partial cross sectional view similar to FIG. 2 of a third embodiment of the present invention.

In the third embodiment illustrated in FIG. 3, an even better air seal between the rotating and stationary parts is achieved by a stepped design of a sleeve 33 accepting the tool shaft in combination with a sleeve 34 connected to the stationary housing part 11. The sleeve 33 corresponds in function to the sleeve 32 of FIG. 2 and is part of the chucking fixture 4 that rotates together with the hollow shaft 5. Whereas essentially planar sealing surfaces that form the sealing gap 30 are provided in the embodiment of FIG. 2, the air seal in the embodiment of FIG. 3 is essentially achieved by narrow gaps 36 and 37 formed by cylindrical surfaces of the tube or sleeve 34 coacting with the surface of the member 33 and the tube 12 coacting with the bore and the member 33. Radial gaps 38, 39 and 40 are provided and are selected to be large as a result whereas the aforementioned undesired pump effect, which particularly occurs at extremely high speeds, will be avoided. The delivery of the compressed air in this version also occurs via a distributor space 35 connected to the compressed air line 13.

Figure 4:
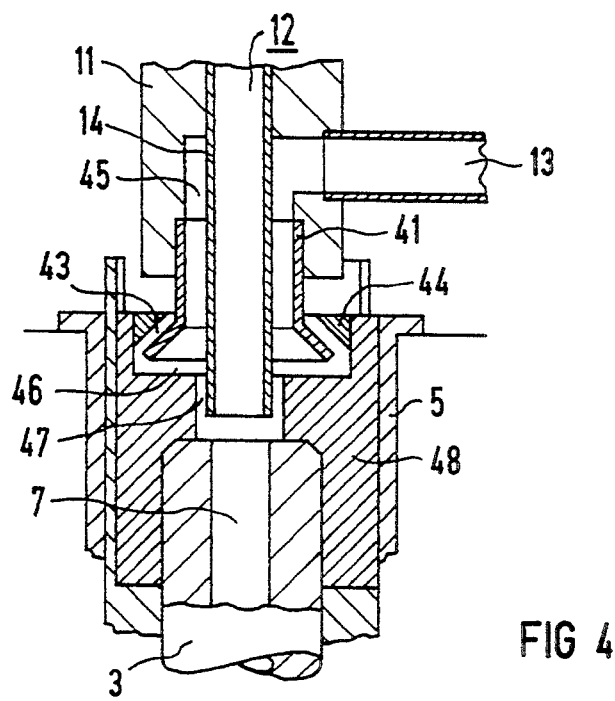
FIG. 4 is a partial cross sectional view similar to FIG. 2 of a fourth embodiment of the present invention.
Figure 5:
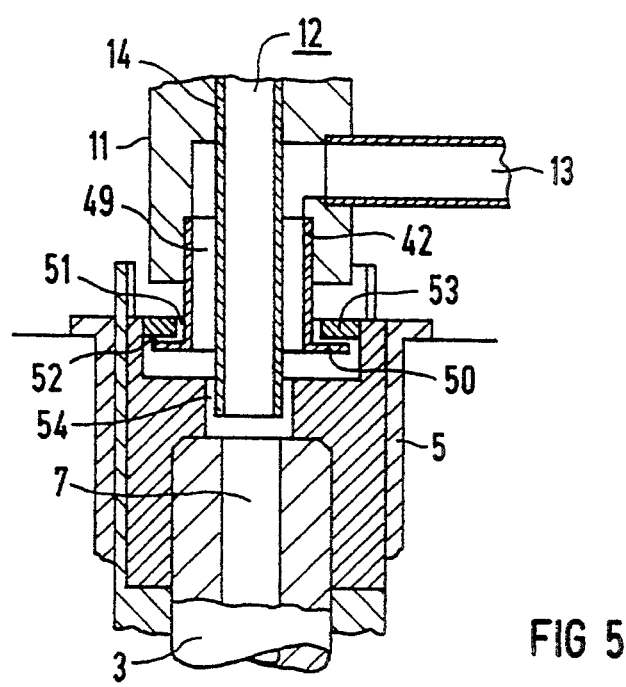
FIG. 5 is a partial cross sectional view of a fifth embodiment of the present invention.

In the embodiments 4 and 5 shown in FIGS. 4 and 5, air guide sleeves 41 and 42 for the coolant are provided concentrically to the delivery channel 12, and these air guide channels 41 and 42 are shaped such that they face toward the admission opening and provide a labyrinth-like deflection of the sealing air.

In the fourth embodiment of FIG. 4, the air guide sleeve 41 comprises an end that cortically expands in an outward direction and which has a correspondingly fashioned ring 44 residing opposite in a corresponding fashion and forms a narrow sealing gap 43. The ring 44 is a component part of the rotating system, i.e., the chucking fixture 4. The air supplied via the compressed air line 13 first enters into the relatively broad distributor space 45 and then charges, first, the sealing gap 43 via a radial gap 46 and, then, secondly, the axially parallel gap 47 which is formed between the end of the section 14 of the delivery line 12 and a bore in the sleeve 48 which corresponds in function to the sleeve 33 of embodiment 3 (FIG. 3).

In the fifth embodiment of FIG. 5, the air guide sleeve 42 comprises a flange-like end 50 opposite which an annular part 53, which is part of the rotating system resides to form an axial sealing gap 51 and a radial gap 52. Here, too, the gaps 51 and 52 serve the purpose of sealing from the outside air and the gap 54 serves the purpose of sealing from the supplied coolant. This embodiment has the distributor space 49.

The embodiments of FIGS. 4 and 5 have the advantage that a high counter-pressure is achieved in the sealing gaps due to the structure of the air seals. In the version of FIG. 5, the radial gap 52 is intentionally selected to be narrower in order to, thus, achieve a pump effect in the direction of compressed air delivery 13 and the distributor space 49. A multi-step structure of such a labyrinth-like flange and sealing gap arrangement is especially advantageous. The air consumption for sealing the gap can, thus, be further reduced.

The supplied coolant, i.e., water, can be connected parallel to the compressed air supply for the sealing air which air is in a line with a first control valve 56. It is especially advantageous when the turn-on of the coolant occurs dependent on the compressed air for sealing the gaps. To accomplish this, these control means include switch means dependent on the compressed air advantageously arranged in the control means or instrument. The switch means can contain a membrane switch valve 57 which, for example, is switched by the change in pressure when the tool is introduced, and this will result in the possibility of establishing an operating of the instrument without the inside parts of the head housing, particularly the collet chuck parts being moistened by emerging cooling water. Such a possibility is established, for example, in the version illustrated in FIG. 1.

Since it is standard in dental instruments to also spray the tool from the outside with cooling water and cooling air or, respectively, with an air/water mixture or spray to which end an appropriate discharge channel is provided in the region of the tool exit at the head housing. It can be advantageous for specific tasks to provide a discharge nozzle 55 for this specific task and to provide a switchover means in the control means by which it is possible to optionally control the water delivery for inside or outside cooling, for example to alternately shut off the delivery line 12 or the line to the nozzle 55. It thereby becomes possible to operate the instrument optionally with inside or outside cooling and also with the inside cooling and with a spray delivered to the outside.

Although various minor modifications may be suggested by those versed in the art, it should be understood that I wish to embody within the scope of the patent granted hereon all such modifications as reasonably and properly come within the scope of my contribution to the art.

I claim:

1. A medical instrument comprising a head housing having means for mounting a hollow shaft for rotation in the housing, said shaft having chucking means with rotating parts for gripping one end of an internally-cooled tool, said tool having an axially-extending channel extending from an admission opening at the one end to an exit opening adjacent the opposite end of the tool, said housing having a first delivery channel connected to a source of coolant and having an exit opening residing opposite the admission opening of the tool in the chucking means in a non-contacting manner, sealing gaps being provided between the rotating parts of the chucking means adjacent the one end of the tool, and a second delivery channel extending concentric relative to the first delivery channel being connected to a source of compressed air under high pressure in comparison to the pressure of the coolant to supply compressed air to the sealing gaps to prevent leakage of the coolant.

2. A medical instrument according to claim 1, wherein sealing gaps are produced by a tubular part that lengthens the tool shaft, said tubular part concentrically surrounding an end section of the first delivery channel for the coolant and, together with parts of the head housing, forming axially parallel and radial sealing gaps.

3. A medical instrument according to claim 2, wherein the tubular part is a small tube which concentrically surrounds the line section of the coolant delivery channel and is put in place on the shaft end of the tool.

4. A medical instrument according to claim 1, wherein a line section of the first delivery channel ends immediately proximate to the one end of the tool shaft so that an exit opening of the coolant line section is defined by a narrow spacing from the admission opening of the tool shaft and wherein a sealing gap formed by cylindrical surfaces is present between a sleeve of the chucking means holding the one end of the tool and the end of the line section of the first delivery channel, wherein sealing gaps formed by the cylindrical surfaces merge into radial-extending sealing gaps which are in communication with the atmosphere via aeration chambers and channels.

5. A medical instrument according to claim 4, wherein the sealing gaps formed by the cylindrical surfaces have a gap width smaller than a gap width of the radial-extending sealing gaps.

6. A medical instrument according to claim 1, which has an air guide sleeve concentrically surrounding a delivery channel for the coolant, said air guide sleeve being shaped with an end facing toward the admission opening providing a labyrinth-like deflection of the outflowing compressed air to the sealing gaps.

7. A medical instrument according to claim 6, wherein the air guide sleeve comprises a conically outwardly expanded end which coacts with a correspondingly fashioned part of the chucking means to form one of the sealing gaps.

8. A medical instrument according to claim 6, wherein the air guide sleeve has a radially extending flange at one end coacting with an inwardly extending fashioned part of the chucking means to form radial and axial sealing gaps.

9. A medical instrument according to claim 1, wherein the head housing is provided with a distributor chamber for receiving the compressed air before entry of the compressed air into the sealing gaps.

10. A medical instrument according to claim 1, which includes a control valve which controls the switching of the compressed air to be switched parallel with the delivery of the coolant.

11. A medical instrument according to claim 1, which includes a control means having a switch valve with which the deliver,/of coolant can be controlled and is arranged in a delivery channel of the coolant.

12. A medical instrument according to claim 11, wherein the head housing includes an additional delivery channel for a coolant which directs the coolant on the outside of a working surface of the tool, said control means includes a control valve with which the delivery of coolant to either the first channel or the additional delivery channel or to both channels can be optionally controlled.

13. A medical instrument according to claim 12, wherein a membrane switch valve which is operated with compressed air is provided as a control valve for the coolant in the control means.

14. A medical instrument according to claim 13, wherein the switching of the control valve occurs due to an increase in pressure in the delivery channel upon introduction of the tool into the chucking means.

15. A medical instrument according to claim 1, wherein the sealing gaps provide a labyrinth-like arrangement.

16. A medical instrument according to claim 15, wherein the labyrinth-like arrangement is a sealing gap arrangement with multiple steps.

17. A medical instrument according to claim 1, wherein sealing gaps are produced by tubular part that lengthens the tool shaft, said tubular part (8) having an end being arranged concentrically and opposite to the exit opening of said first delivery channel, and, together with parts of the head housing, forming axially parallel and radial sealing gaps.

* * * * *